United States Patent
Babish et al.

(10) Patent No.: US 6,979,470 B2
(45) Date of Patent: Dec. 27, 2005

(54) CURCUMINOID COMPOSITIONS EXHIBITING SYNERGISTIC INHIBITION OF THE EXPRESSION AND/OR ACTIVITY OF CYCLOOXYGENASE-2

(75) Inventors: John G. Babish, Brooktondale, NY (US); Terrence Howell, Dryden, NY (US); Linda Pacioretty, Brooktondale, NY (US)

(73) Assignee: Metaproteomics, LLC, San Clemente, CA (US)

( * ) Notice: Subject to any disclaimer, the term of this patent is extended or adjusted under 35 U.S.C. 154(b) by 0 days.

(21) Appl. No.: 10/198,277

(22) Filed: Jul. 16, 2002

(65) Prior Publication Data

US 2003/0108628 A1 Jun. 12, 2003

Related U.S. Application Data

(60) Provisional application No. 60/306,055, filed on Jul. 17, 2001.

(51) Int. Cl.$^7$ ............................................. A61K 35/78
(52) U.S. Cl. ..................... 424/756; 424/725; 435/189; 514/461; 514/679; 514/763
(58) Field of Search .................. 424/725; 435/189; 514/461, 679, 763

(56) References Cited

U.S. PATENT DOCUMENTS

| | | | |
|---|---|---|---|
| 5,314,877 A | * | 5/1994 | Suzuki et al. |
| 5,610,175 A | * | 3/1997 | Vogel et al. |
| 5,910,307 A | * | 6/1999 | Kwak et al. |
| 6,210,701 B1 | | 4/2001 | Darland et al. |
| 6,264,995 B1 | * | 7/2001 | Newmark et al. |

FOREIGN PATENT DOCUMENTS

JP          06009479 A  *  6/1994

OTHER PUBLICATIONS

Amroyan et al. (Phytomedicine (1999), vol. 6, No. 1, ppl. 27–31).*
Zhang et al. (Carcinogenesis (1999), vol. 20, No. 3, pp. 445–451).*
CAPLUS English abstract of Deng et al. (Yaoxue Tongbao (1982), vol. 17. No. 4, pp. 195–198).*
Database CAPLUS on ACS. Accession No. 1982:555926, Deng et al., "Comparison of Pharmacological effect of four andrographolides." Yaoxue Tongbao, 1982, vol. 17, No. 4, pp. 195–198, see English abstract.
P. Bremner, et al., "Natural Products as Targeted Modulators of the Nuclear Factor– κB Pathway," *Journal of Pharmacy and Pharmacology*, 2002, vol. 54: pp. 453–472.
A. Lopes Vaz, "Double–Blind Clinical Evaluation of the Relative Efficacy of Ibuprofen and Glucosamine Sulphate in the Management of Osteoarthrosis of the Knee in Out–Patients," *Current Medical Research and Opinion*, vol. 8, No. 3, 1982, pp. 145–149.

* cited by examiner

*Primary Examiner*—Susan D. Coe
(74) *Attorney, Agent, or Firm*—Simona A. Levi-Minzi; McDermott Will & Emery LLP

(57) ABSTRACT

Compositions comprising an effective amount of a curcuminoid species and an effective amount of a diterpene lactone species, a triterpene species or derivatives thereof that have a synergistic effect on specific inhibition of inducible COX-2 activity and have minimal effect on COX-1 activity are disclosed. Methods of using the compositions for providing synergistic anti-inflammatory effects are also disclosed.

16 Claims, 3 Drawing Sheets

[A]

[B]

[C]

[D]

[E]

[F]

[A]

[B]

[A]

[B]

[C]

CURCUMINOID COMPOSITIONS EXHIBITING SYNERGISTIC INHIBITION OF THE EXPRESSION AND/OR ACTIVITY OF CYCLOOXYGENASE-2

CROSS REFERENCE TO RELATED APPLICATION

This application claims benefit of U.S. Provisional application filed Jul. 17, 2001, Ser. No. 60/306,055.

FIELD OF THE INVENTION

The present invention relates generally to a composition exhibiting synergistic inhibition of the expression and/or activity of inducible cyclooxygenase-2 (COX-2). More particularly, the composition comprises, as a first component, a curcuminoid species and, as a second component, at least one member selected from the group consisting of a diterpene lactone species, and a triterpene species or derivatives thereof. The composition functions synergistically to inhibit the inducibility and/or activity of inducible cyclooxygenase (COX-2) with little or no significant effect on constitutive cyclooxygenase (COX-1).

BACKGROUND OF THE INVENTION

Inflammatory diseases affect more than fifty million Americans. As a result of basic research in molecular and cellular immunology over the last ten to fifteen years, approaches to diagnosing, treating and preventing these immunologically-based diseases has been dramatically altered. One example of this is the discovery of an inducible form of the cyclooxygenase enzyme. Constitutive cyclooxygenase (COX), first purified in 1976 and cloned in 1988, functions in the synthesis of prostaglandins (PGs) from arachidonic acid (AA). Three years after its purification, an inducible enzyme with COX activity was identified and given the name COX-2, while constitutive COX was termed COX-1.

COX-2 gene expression is under the control of pro-inflammatory cytokines and growth factors. Thus, the inference is that COX-2 functions in both inflammation and control of cell growth. While COX-2 is inducible in many tissues, it is present constitutively in the brain and spinal cord, where it may function in nerve transmission for pain and fever. The two isoforms of COX are nearly identical in structure but have important differences in substrate and inhibitor selectivity and in their intracellular locations. Protective PGs, which preserve the integrity of the stomach lining and maintain normal renal function in a compromised kidney, are synthesized by COX-1. On the other hand, PGs synthesized by COX-2 in immune cells are central to the inflammatory process.

The discovery of COX-2 has made possible the design of drugs that reduce inflammation without removing the protective PGs in the stomach and kidney made by COX-1. Component combinations which comprise the compositions of the invention would be useful for, but not limited to, the treatment of inflammation in a subject, and for treatment of other inflammation-associated disorders, such as, as an analgesic in the treatment of pain and headaches, or as an antipyretic for the treatment of fever. For example, component combinations would be useful to treat arthritis, including but not limited to rheumatoid arthritis, spondyloathopathies, gouty arthritis, osteoarthritis, systemic lupus erythematosus, and juvenile arthritis. Such component combinations would also be useful in the treatment of asthma, bronchitis, menstrual cramps, tendonitis, bursitis, and skin related conditions such as psoriasis, eczema, bums and dermatitis. Component combinations as disclosed herein also would be useful to treat gastrointestinal conditions such as inflammatory bowel disease, Crohn's disease, gastritis, irritable bowel syndrome and ulcerative colitis and for the prevention or treatment of cancer such as colorectal cancer. Further, component combinations, making up the compositions of this invention would be useful in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia and the like.

The compositions of the present invention would also be useful in the treatment of ophthalmic diseases, such as retinopathies, conjunctivitis, uveitis, ocular photophobia, and of acute injury to the eye tissue. The combined component compositions would also be useful in the treatment of pulmonary inflammation, such as that associated with viral infections and cystic fibrosis. The combinations of components would also be useful for the treatment of certain nervous system disorders such as cortical dementias, including Alzheimer's disease. Component combinations of the invention are useful as anti-inflammatory agents, such as for the treatment of arthritis, with the additional benefit of having significantly less harmful side effects. As inhibitors of COX-2 mediated biosynthesis of PGE2, these compositions would also be useful in the treatment of allergic rhinitis, respiratory distress syndrome, endotoxin shock syndrome, atherosclerosis, and central nervous system damage resulting from stroke, ischemia and trauma.

Besides being useful for human treatment, these compositions are also useful for treatment of other animals, including horses, dogs, cats, birds, sheep, pigs, etc. An ideal formulation for the treatment of inflammation would inhibit the induction and activity of COX-2 with little effect on the activity of COX-1. Historically, the non-steroidal and steroidal anti-inflammatory drugs used for treatment of inflammation lack the specificity of inhibiting COX-2 without affecting COX-1. Therefore, most anti-inflammatory drugs damage the gastrointestinal system when used for extended periods.

An ideal formulation for the treatment of inflammation would inhibit the induction and activity of COX-2 without affecting the activity of COX-1. However, conventional non-steroidal and steroidal anti-inflammatory drugs lack the specificity of inhibiting COX-2 without affecting COX-1 and cause damages on the gastrointestinal system when used for extended periods.

A yellow pigmented fraction isolated from the rhizomes of *Curcuma longa* contains curcuminoids belonging to the dicinnamoyl methane group. Curcuminoids are present to the extent of 3 to 5 percent. They are considered the most important active ingredients and are believed to be responsible for the biological activity of *Curcuma longa*. Though their major activity is anti-inflammatory, curcuminoids have been reported to possess antioxidant, antiallergic, wound healing, antispasmodic, antibacterial, antifungal and antitumor activity as well. Curcumin (FIG. 1B) was isolated in 1815 and structurally defined in 1910. Other curcuminoids isolated from *Curcum longa* include demethoxycurcumin (FIG. 1C), bisdemethoxycurcumin (FIG. 1D), a cis-trans geometrical isomer of curcumin (FIG. 1E), and cyclocurcumin (FIG. 1F). Curcuminoids may be found in other botanicals in addition to *Curcuma longa*, such as *Curcuma xanthorrhiza* and *Curcuma zedoaria*.

Curcuminoids are well known for their anti-inflammatory activity. Tumeric is one of the oldest anti-inflammatory drugs used in Ayurvedic medicine. The anti-inflammatory activity of curcuminoids has been evaluated in inflammatory reaction models such as chemical or physical irritants like carrageenin, cotton pellets, formaldehyde and the granuloma pouch. Human, double-blinded, clinical trials have demonstrated efficacy in rheumatoid arthritis at a dose of 1200 mg curcuminoids/day for five to six weeks. At these doses, however, signs of gastrointestinal (GI) discomfort and stomach irritation are frequently reported.

The GI upset and stomach irritation caused by high doses of curcuminoids may be due to the fact that curcuminoids act on prostaglandin production in a manner similar to that of aspirin and aspirin-like anti-inflammatory agents. Numerous studies have shown that the relative incidence of these GI side effects can be correlated to the relative COX-2 specificity of these agents. The higher the specificity for COX-2 over COX-1, the lower the incidence of GI upsets. Thus, aspirin, with a COX-2 specificity of only 0.6, produces a greater incidence of GI distress than curcuminoids, with a reported COX-2 specificity of nearly 3.0. However, the generally accepted COX-2 specificity necessary to significantly reduce the probability of GI upsets is 5.0. Thus, combinations of curcuminoids and other compounds or botanical extracts that increase the COX-2 specificity of curcuminoids would provide a novel and improved anti-inflammatory composition.

Diterpene lactone species, such as andrographolide, and triterpene species, such as ursolic acid and oleanolic acid, are commonly found in plants and are used for their anti-inflammatory properties. The anti-inflammatory effects of these compounds have been described in the literature since 1960. Their mechanism of action is believed to be due (i) to the inhibition of histamine release from mast cells or (ii) to the inhibition of lipoxygenase and cyclooxygenase activity thereby reducing the synthesis of inflammatory factors produced during the arachidonic acid cascade. In addition, andrographolide and oleanolic are potent antioxidants, capable of inhibiting the generation of reactive oxygen intermediates and restoring tissue glutathione levels following stress.

Compositions comprising combinations of botanicals containing curcuminoids and diterpene lactones or triterpenoids have not been described in either traditional or commercial medicine. Thus, it would be useful to identify a composition that would specifically enhance the anti-inflammatory effect of curcuminoids so that they could be used at sufficiently low doses or at current clinical doses with no adverse side effects. An optimal formulation of curcuminoids for preserving the health of joint tissues, for treating arthritis or other inflammatory conditions with high COX-2 specificity (>5-fold) has not yet been discovered. A formulation combining curcuminoids and a second compound to synergistically inhibit COX-2 with high specificity and support the normalization of joint function has not yet been described or discovered.

Thus, it would be useful to identify a natural formulation of compounds that would specifically inhibit or prevent the synthesis of prostaglandins by COX-2 with little or no effect on COX-1. Such a formulation, which would be useful for preserving the health of joint tissues, for treating arthritis or other inflammatory conditions, has not previously been discovered. The term "specific or selective COX-2 inhibitor" embraces compounds or mixtures of compounds that selectively inhibit COX-2 over COX-1. Preferably, the compounds have a median effective concentration for COX-2 inhibition that is minimally five times greater than the median effective concentration for the inhibition of COX-1. For example, if the median inhibitory concentration for COX-2 of a test formulation was 0.2 $\mu$g/mL, the formulation would not be considered COX-2 specific unless the median inhibitory concentration for COX-1 was equal to or greater than 1 $\mu$g/mL.

While glucosamine is generally accepted as being effective and safe for treating osteoarthritis, medical intervention into the treatment of degenerative joint diseases is generally restricted to the alleviation of its acute symptoms. Medical doctors generally utilize non-steroidal and steroidal anti-inflammatory drugs for treatment of osteoarthritis. These drugs, however, are not well-adapted for long-term therapy because they not only lack the ability to promote and protect cartilage, they can actually lead to degeneration of cartilage or reduction of its synthesis. Moreover, most non-steroidal, anti-inflammatory drugs damage the gastrointestinal system when used for extended periods. Thus, new treatments for arthritis are urgently needed.

The joint-protective properties of glucosamine would make it an attractive therapeutic agent for osteoarthritis except for two drawbacks: (i) the rate of response to glucosamine treatment is slower than for treatment with anti-inflammatory drugs, and (ii) glucosamine may fail to fulfill the expectation of degenerative remission. In studies comparing glucosamine with non-steroidal anti inflammatory agents, for example, a double-blinded study comparing 1500 mg glucosamine sulfate per day with 1200 mg ibuprofen, demonstrated that pain scores decreased faster during the first two weeks in the ibuprofen patients than in the glucosamine-treated patients. However, the reduction in pain scores continued throughout the trial period in patients receiving glucosamine and the difference between the two groups turned significantly in favor of glucosamine by week eight. Lopes Vaz, A., *Double-blind clinical evaluation of the relative efficacy of ibuprofen and glucosamine sulphate in the management of osteoarthritis of the knee in outpatients*, 8 Curr. Med Res Opin. 145–149 (1982). Thus, glucosamine may relieve the pain and inflammation of arthritis, but at a slower rate than the available anti-inflammatory drugs.

An ideal formulation for the normalization of cartilage metabolism or treatment of osteoarthritis would provide adequate chondroprotection with potent anti-inflammatory activity. The optimal dietary supplement for osteoarthritis should enhance the general joint rebuilding qualities offered by glucosamine and attenuate the inflammatory response without introducing any harmful side effects. It should be inexpensively manufactured and comply with all governmental regulations.

However, the currently available glucosamine formulations have not been formulated to optimally attack and alleviate the underlying causes of osteoarthritis and rheumatoid arthritis. Moreover, as with many commercially-available herbal and dietary supplements, the available formulations do not have a history of usage, nor controlled clinical testing, which might ensure their safety and efficacy.

Therefore, it would be useful to identify a composition that would specifically inhibit or prevent the expression of COX-2 enzymatic activity, while having little or no effect on COX-1 metabolism so that these could be used at sufficiently low doses, or at current clinical doses, with no significant adverse side effects.

SUMMARY OF THE INVENTION

The present invention provides a composition comprising, as a first component, a curcuminoid species and, as a second component, a compound that would specifically and synergistically enhance the anti-inflammatory effect of the curcuminoid. The composition comprises a curcuminoid species and at least one member selected from the group consisting of an active diterpene lactone species, and a triterpene species or derivatives thereof. Any curcuminoid, diterpene lactone or triterpene species is inclusive of derivatives of the respective genus. However, additional species or mixtures of species within the various genera may be present in the composition which is limited in scope only by the combinations of species within the various genera that exhibit the claimed synergistic functionality. The composition functions synergistically to inhibit the inducibility and/or activity of COX-2 with little or no effect on COX-1. The present invention further provides a composition of matter to increase the rate at which glucosamine or chondroitin sulfate function to normalize joint movement or reduce the symptoms of osteoarthritis.

One specific embodiment of the present invention is a composition comprising an effective amount of curcumin and at least one compound selected from the group consisting of andrographolide, ursolic acid and oleanolic acid.

The present invention also provides a method of dietary supplementation and a method of treating inflammation or inflammation-based diseases in an animal which comprises providing to the animal suffering symptoms of inflammation the composition of the present invention containing a second component which specifically and synergistically enhances the anti-inflammatory effect of the first component, a curcuminoid, and continuing to administer such a dietary supplementation of the composition until said symptoms are eliminated or reduced.

DETAILED DESCRIPTION OF THE INVENTION

Figure 1:
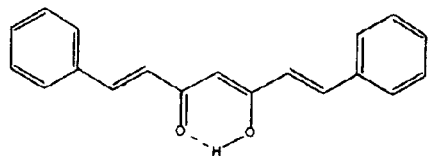
FIG. 1 illustrates the general chemical structure[A], of the curcuminoid genus and [B], [C], [D], [E] and [F], respectively, as curcumin, demethoxycurcumin bisdemethoxycurcumin, the cis-trans geometrical isomer of curcumin, and cyclocurcumin as species within that genus.
Figure 1:
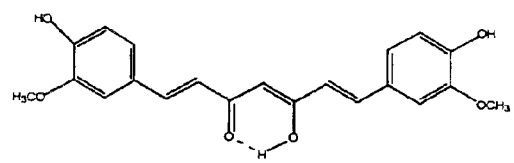
Figure 1:
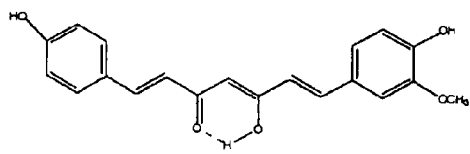
Figure 1:
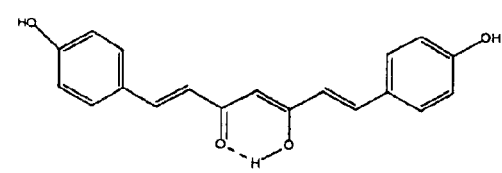
Figure 1:
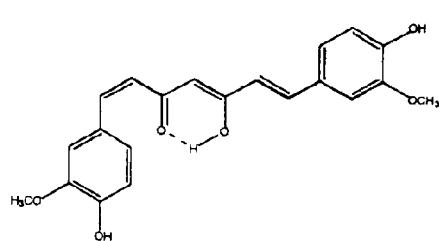
Figure 1:
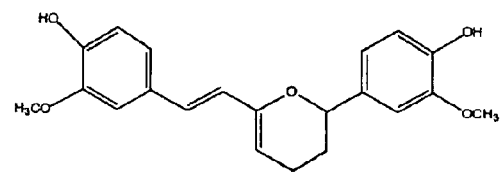

Before the present composition and methods of making and using thereof are disclosed and described, it is to be understood that this invention is not limited to the particular configurations, as process steps, and materials may vary somewhat. It is also intended to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

The present invention provides a composition having a synergistic inhibitory effect on the expression and/or activity of COX-2. More particularly, the composition comprises, as a first component, an active curcuminoid and, as a second component, at least one member selected from the group consisting of an active diterpene lactone or triterpene or derivatives thereof as more specifically described above. The composition provided by the present invention can be formulated as a dietary supplement or therapeutic composition. The composition functions synergistically to inhibit the inducibility and/or activity of COX-2 with no significant effect on COX-1.

As used herein, the term "dietary supplement" refers to compositions consumed to affect structural or functional changes in physiology. The term "therapeutic composition" refers to any compounds administered to treat or prevent a disease.

As used herein, the term "active curcuminoid", diterpene lactones, and triterpenes or derivatives thereof refers to naturally occurring or synthetic derivatives of species within the scope of the respective genera that is capable of inhibiting the inducibility and/or activity of COX-2 while having little or no effect on COX-1 or is capable of inhibiting or reducing the severity of an inflammatory response. Representative species within each genus are listed in Table 1. Of the species listed under each genus in Table 1, those containing at least one asterisk (*) are preferred and those containing two asterisks (**) are particularly preferred.

TABLE 1

| CURCUMINOIDS | DITERPENE LACTONES | TRITERPENES |
|---|---|---|
| Curcumin** | Andrographolide** | 18-a-Glycyrrhetinic acid** |
| Demethoxycurcumin** | Edelin lactone | 18-β-Glycyrrhetinic acid** |
| Bisdemethoxycurcumin** | Selenoandrographolide* | 2-a-3-a-Dihydrooxyurs-12-3n-28-onic acid* |
| Cis-trans curcumin* | Deoxyandrogrpholide** | 3-a-Hydroxyursolic acid* |
| Cyclocurcumin* | Neoandrographolide** | 3-Oxo-ursolic acid* |
| | Andrographan* | Betulin** |
| | Homoandrographolide* | Betulinic acid** |
| | Androgrphosterin* | Celastrol* |
| | 14-deoxy-11-Oxoandrographolide | Eburicoic acid |
| | 14-deoxy-11,12-Didehydroandrographolide | Friedelin* |
| | Andrographiside* | Glycyrrhizin |
| | Andrographon* | Gypsogenin |

TABLE 1-continued

| CURCUMINOIDS | DITERPENE LACTONES | TRITERPENES |
|---|---|---|
| | | Oleanolic acid** |
| | | Oleanolic acid-3-acetate |
| | | Pachymic acid |
| | | Pinicolic acid |
| | | Sophoradiol |
| | | Soyasapogenol A |
| | | Soyasapogenol B |
| | | Tripterin** |
| | | Triptophenolide* |
| | | Tumulosic acid |
| | | Ursolic acid** |
| | | Ursolic acid-3-acetate |
| | | Uvaol* |
| | | β-sitosterol |

"Conjugates" of curcuminoids, diterpene lactones, triterpenes or derivatives thereof means curcuminoids, diterpene lactones, triterpenes covalently bound or conjugated to a member selected from the group consisting of mono- or di-saccharides, amino acids, sulfates, succinate, acetate and glutathione. Preferably, the mono- or di- saccharide is a member selected from the group consisting of glucose, mannose, ribose, galactose, rhamnose, arabinose, maltose, and fructose.

Therefore, one preferred embodiment of the present invention is a composition comprising effective amount of curcumin, as a first component, and a second component selected from the group consisting of andrographolide, ursolic acid and oleanolic acid. The resulting formulation of these combinations functions to synergistically inhibit the inducibility and/or activity of COX-2 while showing little or no effect on COX-1. Therefore, the composition of the present invention essentially eliminates the inflammatory response rapidly without introducing any harmful side effects.

Preferably, the curcuminoid genus, as represented by FIG. 1[A] and specifically exemplified by curcumin in FIG. 1[B] is a pharmaceutical grade botanical extract such as can be obtained commercially, for example, from Sabinsa, 121 Ethel Road West, Piscataway, N.J. Other curcuminoids that may be employed include demethoxycurcumin (FIG. 1[C]) bisdemethoxycurcumin (FIG. 1[D]), cis-trans curcumin (FIG. 1E) and cyclocurcumin (FIG. 1F). The curcuminoid used can be readily obtained from *Curcuma longa* L. Pharmaceutical grade curcuminoid extract is standardized to have a curcuminoid content of greater than 70 percent. The pharmaceutical, botanical grade extract must pass extensive safety and efficacy procedures. As employed in the practice of the present invention, the extract has a curcuminoid content of about 1 to 99 percent by weight. Preferably, the minimum curcumin content is about 70 percent by weight. Alternatively, the curcumin may be synthesized using standard techniques known in chemical synthesis.

The essence of the present invention is that, rather than modifying the curcuminoid molecules to achieve greater efficacy and lower toxicity, a second component is added that acts in a synergistic manner. Therefore, this invention relates to the discovery that when combining at curcuminoid with a second molecule, selected from the group consisting of a diterpene lactone, a triterpene and derivatives thereof, the combination produces a synergistic effect in the target cell. One such synergistic response would be the specific inhibition of inducible COX-2. Preferably, the second molecule is a member selected from the group consisting of andrographolide, ursolic acid and oleanolic acid.

Figure 2:
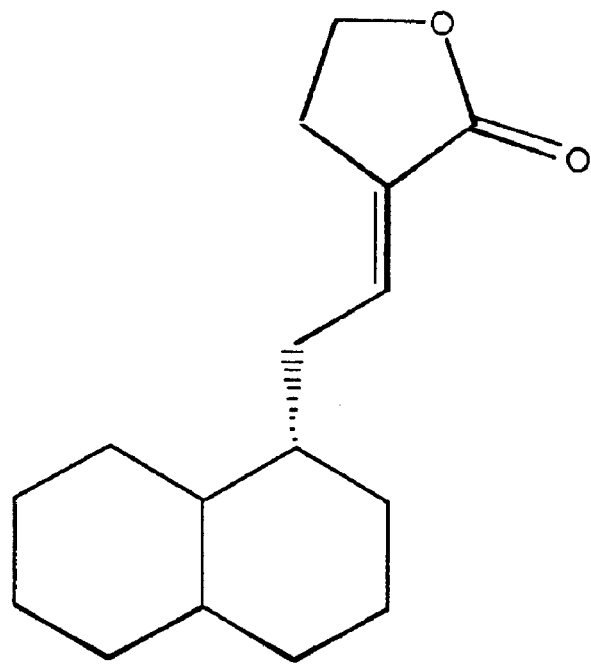
FIG. 2,[A] and [B] respectively, illustrate the general chemical structures of the diterpene lactone genus and andrographolide as a species within that genus.
Figure 2:
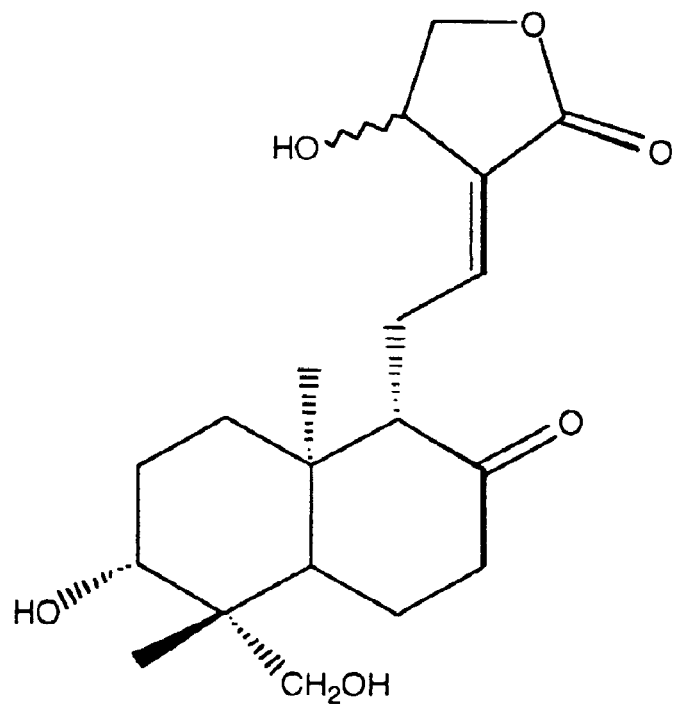
Figure 3:
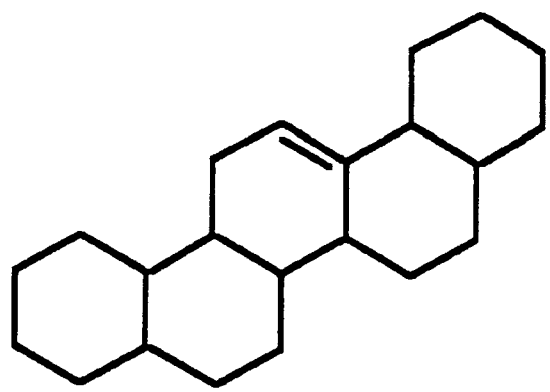
FIG. 3[A], [B] and [C] respectively, illustrate the general chemical structures of the triterpene genus and ursolic acid and oleanolic acid as a species within that genus.
Figure 3:
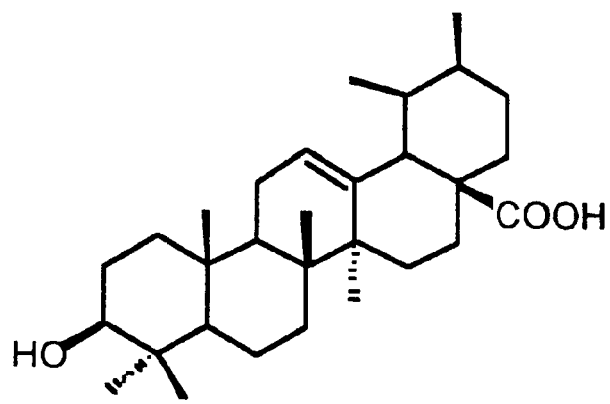
Figure 3:
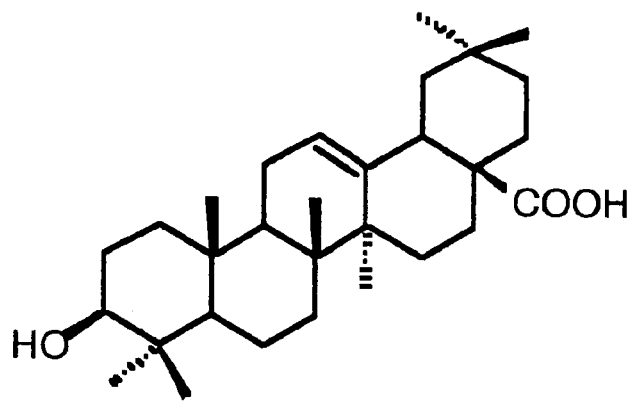

Preferably, the diterpene lactone genus, as represented by FIG. 2[A] and specifically by andrographolide in FIG. 2[B], and the tripterpene genus, as represented by FIG. 2[A] and specifically exemplified by ursolic acid (FIG. 2[B]) or oleanolic acid (FIG. 2[C]) as species is a pharmaceutical grade preparation such as can be obtained commercially, for example, from Garden State Nutritionals, 8 Henderson Drive, West Caldwell, N.Y. 07006. Andrographolide can be obtained from *Andrographis paniculata*, while both ursolic and oleanolic acid are found in a wide variety of botanicals. For example, botanical sources for ursolic acid can be selected from the group consisting of from *Adina piluifera, Agrimonia eupatoria, Arbutus unedo, Arctostaphylos uva-ursi, Artocarpus heterophyllus, Catalpa bignoniodes, Catharanthus roseus, Chimaphila umbellata, Cornus florida, Cornus officinalis, Crataegus cuneata, Crataegus laevigata, Crataegus pinnatifida, Cryptostegia grandifolia, Elaeagnus pungens, Eriobotrya japonica, Eucalyptus citriodora, Forsythia suspensa, Gaultheria fragrantissima, Glechoma hederacea, Hedyotis diffusa, Helichrysum angustifolium, Humulus lupulus, Hyssopus officinalis, Ilex paraguariensis, Lavandula angustifolia, Lavandula latifolia, Leonurus cardiaca, Ligustrum japonicum, Limonia acidissima, Lycopus europeus, Malus domestica, Marubium vulgare, Melaleuca leucadendra, Melissa officinalis, Mentha spicata, Mentha x rotundifolia, Monarda didyma, Nerium oleander, Ocimum basilicum, Ocimum basilicum, Ocimum basilicum, Ocimum baslicum, Ocimum canum, Origanum majorana, Origanum vulgare, Plantago asiatica, Plantago major, Plectranthus amboinicus, Prunell vulgaris, Prunella vulgaris, Prunus cerasus, Prunus laurocerasus, Prunus persica, Prunus serotina* spp *serotina, Psidium guajava, Punica granatum, Pyrus communis, Rhododendron dauricum, Rhododendron ferrugineum, Rhododendron ponticum, Rosmarinus officinalis, Rubus fruticosus, Salvia officinalis, Salvia sclarea, Salvia triloba, Sambucus nigra, Sanguisorba officinalis, Satureja hortensis, Satureja montana, Sorbus aucubaria, Syringa vulgaris, Teucrium chamaedrys Teucrium polium, Teucrium* spp, *Thevetia peruviana, Thymus serpyllum, Thymus vulgaris, Uncaria tomentosa, Vaccinium corymobosum, Vaccinium myrtillus, Vaccinium vitis idaea, Verbena officinalis, Viburnum opulus* var. *opulus, Viburnum prunifolium, Vinca minor* or *Zizyphus jujuba*. Similarly, oleanolic acid is found in *Achyranthes aspera, Achyranthes bidentiata, Adina piluifera, Ajpocynum cannabinum, Akebia quinata, Allium cepa, Allium sativum, Arctostaphylos uva-ursi, Calendula officinalis, Catharanthus roseus, Centaurium erythraea, Chenopodium album, Citrullus colocynthis, Cnicus benedictus, Cornus officinalis, Crataegus pinnatifida Cyperus rotundus, Daemonorops*

*draco, Diospyros kaki, Elaeagnus pungens, Eleutherococcus senticosus, Eriobotrya japonica, Eugenia caryophyllata, Forsythia suspensa, Glechoma hederacea, Harpagophtum procumbens, Hedera helix, Hedyotis diffusa, Helianthus annuus, Hemsleys amabilis, Humulus lupulus, Hyssopus officinalis, Ilex rotunda, Lavandula latifolia, Leonurus cardiaca, Ligustrum japonicum, Ligustrum lucidum, Liquidambar orientalis, Liquidambar styraciflua, Loranthus parasiticus, Luffa aegyptiaca, Melaleuca leucadendra, Melissa officinalis, Mentha spicata, Mentha x rotundifolia, Momordica cochinchinensis, Myristica fragrans, Myroxylon balsamum, Nerium oleander, Ocimum suave, Ociumum basilicum, Olea europaea, Origanum majorana, Origanum vulgare, Paederia scandens, Panax ginseng, Panax japonicus, Panax quinquefolius, Patrinia scabiosaefolia, Phytolacca americana, Plantago major, Plectranthus amboinicus, Prunella vulgaris, Prunus cerasus, Psidium guajava, Pulsatilla chinenisis, Quisqualis indica, Rosmarinus officinalis, Salvaia officinalis, Salvia sclarea, Salvia triloba, Sambucus nigra, Satureja hortensis, Satureja montana, Swertia chinensis, Swertia diluta, Swertia mileensis, Syzygium aromaticum, Thymus serpyllum, Thymus vulgaris, Trachycarpus fortunei, Uncaria tomentosa, Vaccinium corymbosum, Vaccinium myrtillus, Viburnum prunifolium, Viscum album, Vitis vinifera,* and *Zizyphus jujuba.*

The preferred botanical sources for ursolic acid is a member selected from the group consisting of *Ligustrum japonicum, Plantago asiatica, Plantago major, Prunus* species, *Uncaria tomentosa, Zizyphus jujuba, Cornus officinalis, Eucalyptus citriodora, Forsythia suspensa, Lavandula latifolia, Malus domestica, Nerium oleander, Ocimum baslicum, Punica granatum, Pyrus communis, Rosmarinus officinalis, Salvia triloba, Sorbus aucubaria, Vaccinium myrtillus, Vaccinium vitis-idaea,* and *Viburnum opulus* var. *opulus.* The most preferred botanical sources for ursolic acid is a member selected from the group consisting of *Ligustrum japonicum, Plantago asiatica, Plantago major, Prunus* species, *Uncaria tomentosa,* and *Zizyphus jujuba.*

The preferred botanical source for oleanolic acid is a member selected from the group consisting of *Eleutherococcus senticosus, Ligustrum japonicum, Ligustrum lucidum, Panax ginseng, Panax japonicus, Panax quinquefolius, Plantago major, Prunella vulgaris, Vitis vinifera, Zizyphus jujuba, Achyranthes bidentiata, Allium cepa, Allium sativum, Cornus officinalis, Daemonorops draco, Forsythia suspensa, Prunus cerasus, Quisqualis indica, Rosmarinus officinalis, Salvia triloba, Syzygium aromaticum, Thymus vulgaris, Uncaria tomentosa, Vaccinium corymbosum,* and *Vaccinium myrtillus.* The most preferred botanical source for oleanolic acid is a member selected from the group consisting of *Eleutherococcus senticosus, Ligustrum japonicum, Ligustrum lucidum, Panax ginseng, Panax japonicus, Panax quinquefolius, Plantago major, Prunella vulgaris Vitis vinifera* and *Zizyphus jujuba.*

The pharmaceutical grade extract must pass extensive safety and efficacy procedures. Pharmaceutical grade andrographolide, ursolic acid or oleanolic acid refers to a preparation wherein the concentration of andrographolide, ursolic acid or oleanolic acid is greater than 90 percent by total weight of the preparation. As employed in the practice of the present invention, the extract has a minimum andrographolide, ursolic acid or oleanolic acid content of about 3 to 99 percent by weight. Preferably, the minimum andrographolide, ursolic acid or oleanolic acid content is greater than 10 percent by weight. The pharmaceutical grade extracts are particularly preferred. Without limiting the invention, it is anticipated that andrographolide, ursolic acid or oleanolic acid act to inhibit the generation of reactive oxygen intermediates (ROI) from AA metabolism and thereby prevent an increase in the rate of transcription of the COX-2 gene by the transcriptional regulatory factor NF-kappa B.

Without limiting the invention, the inhibition of the activity of the COX-2 enzyme by the diterpene lactones or triterpenes provides a dual, synergistic effect with curcuminoids. Thus, the second compound selected from the group consisting of diterpene lactones and triterpenes increases the anti-inflammatory activity of the curcuminoids. The result of the combinations of this invention is a more selective effect on the activity of COX-2 at lower doses of curcuminoids than would normally be required. By decreasing the dose of curcuminoids to achieve the desired COX-2 inhibition, the probability of side effects from this compound decreases almost exponentially. The second compound selected from the group consisting of diterpene lactones and triterpenes can provide hepatoprotection, antitumor promotion, antihyperlipidemia, antihyperglycemia, and protection against ulcer formation from COX-1 inhibition by the curcuminoids.

Preferably, a daily dose (mg/kg-day) of the present dietary supplement would be formulated to deliver, per kg body weight of the animal, about 0.001 to 30.0 mg curcuminoids, and about 0.5 to 20.0 mg diterpene lactones or triterpenes.

The composition of the present invention for topical application would contain one of the following: about 0.001 to 1 wt %, preferably 0.01 to 1 wt % curcuminoids, and about 0.025 to 1 wt %, preferably 0.05 to 1 wt % diterpene lactones or triterpenes.

The preferred composition of the present invention would produce serum concentrations in the following range: 0.0001 to 10 $\mu$M of curcuminoids, and 0.001 to 10 $\mu$M of diterpene lactones or triterpenes.

Table 2 below provides a list of diseases in which COX-2 enzyme expression and activity may play a significant role and therefore are appropriate targets for normalization or treatment by the invention.

TABLE 2

| DISEASE | TISSUE |
| --- | --- |
| Addison's Disease | Adrenal |
| Allergies | Inflammatory cells |
| Alzheimer Disease | Nerve cells |
| Arthritis | Inflammatory cells |
| Atherosclerosis | Vessel wall |
| Colon Cancer | Intestine |
| Crohn's Disease | Intestine |
| Diabetes (type I)/type II | Pancreas |
| Eczema | Skin/Inflammatory cells |
| Graves' Disease | Thyroid |
| Guillain-Barre Syndrome | Nerve cells |
| Inflammatory Bowel Disease | Intestine |
| Leukemia | Immune cells |
| Lymphomas | Immune cells |
| Multiple Sclerosis | Nerve cells |
| Myasthenia Gravis | Neuromuscular junction |
| Osteoarthritis | Joint lining |
| Psoriasis | Skin |
| Primary Biliary Cirrhosis | Liver |
| Rheumatoid Arthritis | Joint lining |
| Solid Tumors | Various |
| Systemic Lupus Erythematosis | Multiple tissues |
| Uveitis | Eye |

In addition to the combination of curcuminoids and diterpene lactones, triterpenes or derivatives, the present composition for dietary application may include various additives such as other natural components of intermediary metabolism, vitamins and minerals, as well as inert ingredients such as talc and magnesium stearate that are standard excipients in the manufacture of tablets and capsules.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the present composition is contemplated. In one embodiment, talc and magnesium stearate are included in the present formulation. When these components are added they are preferably Astac Brand 400 USP talc powder and the veritable grade of magnesium stearate. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the present invention can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, the present compositions may also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gumdrops, chewable candies or slowly dissolving lozenges. The present invention contemplates treatment of all types of inflammation-based diseases, both acute and chronic. The present formulation reduces the inflammatory response and thereby promotes healing of, or prevents further damage to, the affected tissue. A pharmaceutically acceptable carrier may also be used in the present compositions and formulations.

According to the present invention, the animal may be a member selected from the group consisting of humans, non-human primates, dogs, cats, birds, horses, ruminants or other warm blooded animals. The invention is directed primarily to the treatment of human beings. Administration can be by any method available to the skilled artisan, for example, by oral, topical, transdermal, transmucosal, or parenteral routes.

The following examples are intended to illustrate but not in any way limit the invention:

EXAMPLE 1

Synergistic Inhibition of Prostaglandin E2 Production in Murine B Cells by Curcuminoids and Andrographolide This example illustrates the superior COX-2 selectivity of the combination of curcuminoids and andrographolide of the present invention compared to curcuminoids described in the prior art.

Inhibition of COX-2 Mediated Production of PGE2 in RAW 264.7 Cells

Equipment—balancer, analytical, Ohaus Explorer (Ohaus Model #EO1140, Switzerland), biosafety cabinet (Forma Model #F1214, Marietta, Ohio), pipettor, 100 to 1000 $\mu$L (VWR Catalog #4000-208, Rochester, N.Y.), cell hand tally counter (VWR Catalog #23609-102, Rochester, N.Y.), $CO_2$ incubator (Forma Model #F3210, Marietta, Ohio), hemacytometer (Hausser Model #1492, Horsham, Pa.), microscope, inverted (Leica Model #DM IL, Wetzlar, Germany), multichannel pipettor, 12-Channel (VWR Catalog #53501-662, Rochester, N.Y.), Pipet Aid (VWR Catalog #53498-103, Rochester, N.Y.), Pipettor, 0.5 to 10 $\mu$L (VWR Catalog #4000-200, Rochester, N.Y.), pipettor, 100 to 1000 $\mu$L (VWR Catalog #4000-208, Rochester, N.Y.), pipettor, 2 to 20 $\mu$L (VWR Catalog #4000-202, Rochester, N.Y.), pipettor, 20 to 200 $\mu$L (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vortex mixer (VWR Catalog #33994-306, Rochester, N.Y.), water bath (Shel Lab Model #1203, Cornelius, Oreg.).

Cells, Chemicals, Reagents and Buffers—Cell scrapers (Corning Catalog #3008, Corning, N.Y.), dimethylsulfoxide (DMSO) (VWR Catalog #5507, Rochester, N.Y.), Dulbecco's Modification of Eagle's Medium (DMEM) (Mediatech Catalog #10-013-CV, Herndon, Va.), fetal bovine serum, heat inactivated (FBS-HI) (Mediatech Catalog #35-011-CV CV, Herndon, Va.), lipopolysaccharide (LPS)(Sigma Catalog #L-2654, St. Louis, Mo.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 $\mu$L pipettor (VWR Catolog #53509-138, Rochester, N.Y.), pipet tips for 100–1000 $\mu$L pipettor (VWR Catolog #53512-294, Rochester, N.Y.), pipet tips for 2–20 $\mu$L and 20–200 $\mu$L pipettors (VWR Catolog #53512-260, Rochester, N.Y.), pipets, 10 mL (Becton Dickinson Catalog #7551, Marietta, Ohio), pipets, 2 mL (Becton Dickinson Catalog #7507, Marietta, Ohio, pipets, 5 mL (Becton Dickinson Catalog #7543, Marietta, Ohio), RAW 264.7 Cells (American Type Culture Collection Catalog #TIB-71, Manassas, Va.), test compounds (liquid $CO_2$ hops extract from Hopunion, Yakima, Wash.), tissue culture plates, 96-well (Becton Dickinson Catalog #3075, Franklin Lanes, N.J.), Ultra-pure water (Resistance=18 megaOhm–cm deionized water).

General Procedure—RAW 264.7 cells, obtained from ATCC, were grown in DMEM medium and maintained in log phase growth. The DMEM growth medium was made as follows: 50 mL of heat inactivated FBS and 5 mL of penicillin/streptomycin were added to a 500 mL bottle of DMEM and stored at 4° C. This was warmed to 37° C. in a water bath before use and for best results should be used within three months.

On day one of the experiment, the log phase 264.7 cells were plated at $8 \times 10^4$ cells per well in 0.2 mL growth medium per well in a 96-well tissue culture plate. After 6 to 8 hours post plating, 100 $\mu$L of growth medium from each well was removed and replaced with 100 $\mu$L fresh medium. A 1.0 mg/mL solution of LPS, which was used to induce the expression of COX-2 in the RAW 264.7 cells, was prepared by dissolving 1.0 mg of LPS in 1 mL DMSO. It was mixed until dissolved and stored at 4° C. Immediately before use, it was thawed at room temperature or in a 37° C. water bath. A new solution was prepared every 60 days.

On day two of the experiment, the test materials were prepared as 1000× stock in DMSO. For example, if the final concentration of the test material was to be 10 µg/mL, a 10 mg/mL stock was prepared by dissolving 10 mg of the test material in 1 mL of DMSO. Fresh test materials were prepared on day 2 of the experiment. In 1.7 mL microfuge tubes, 1 mL DMEM without FBS was added to obtain test concentrations of 0.05, 0.10, 0.5, and 1.0 µg/mL. 2 µL of the 1000×DMSO stock of the test material was added to the 1 mL of medium without FBS. The tube contained the final concentration of the test material was concentrated 2-fold. The tube was placed in incubator for 10 minutes to equilibrate.

One-hundred mL of medium was removed from each well of the cell plates prepared on day one. One-hundred mL of equilibrated 2× final concentration the test compounds were added to cells and incubated for 90 minutes. LPS in DMEM without FBS was prepared by adding 44 µL of the 1 mg/mL DMSO stock to 10 mL of medium. For each well of cells to be stimulated, 20 µL of LPS (final concentration of LPS is 0.4 µg/mL of LPS) was added. The LPS stimulation was continued for 24 hours, after which the supernatant medium from each well was transferred to a clean microfuge tube for determination of the PGE2 content in the medium.

Determination of COX-1 Enzyme Inhibition by Curcuminoids and Andrographolide

The ability of a test material to inhibit COX-1 synthesis of PGE2 was determined essentially as described by Noreen, Y., et al. (J. Nat. Prod. 61, 2–7, 1998).

Equipment—balancer (2400 g, Acculab VI-2400, VWR Catalog #11237-300, Rochester, N.Y.), balancer, analytical, Ohaus Explorer (Ohaus Model #EO1140, Switzerland), biosafety cabinet (Forma Model #F1214, Marietta, Ohio), Freezer, −30° C. (Forma Model #F3797), Freezer, −80° C. Ultralow (Forma Model #F8516, Marietta, Ohio), heated stirring plate (VWR Catalog #33918-262, Rochester, N.Y.), ice maker (Scotsman Model #AFE400A-1A, Fairfax, S.C.), multichannel pipettor, 12-Channel (VWR Catalog #53501-662, Rochester, N.Y.), Multichannel Pipettor, 8-Channel (VWR Catalog #53501-660, Rochester, N.Y.), orbital shaker platform (Scienceware #F37041-0000, Pequannock, N.J.), pH meter (VWR Catalog #33221-010, Rochester, N.Y.), pipet aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vacuum chamber (Sigma Catalog #Z35, 407-4, St. Louis, Mo.), vortex mixer (VWR Catalog #33994-306, Rochester, N.Y.)

Supplies and Reagents—96-Well, round-bottom plate (Nalge Nunc #267245, Rochester, N.Y.), arachidonic acid (Sigma Catalog #A-3925, St. Louis, Mo.), centrifuge tubes, 15 mL, conical, sterile (VWR Catalog #20171-008, Rochester, N.Y.), COX-1 enzyme (ovine) 40,000 units/mg (Cayman Chemical Catalog #60100, Ann Arbor, Mich.), dimethylsulfoxide (DMSO) (VWR Catalog #5507, Rochester, N.Y.), ethanol 100% (VWR Catalog #MK701908, Rochester, N.Y.), epinephrine (Sigma Catalog #E-4250, St. Louis, Mo.), glutathione (reduced) (Sigma Catalog #G-6529, St. Louis, Mo.), graduated cylinder, 1000 mL (VWR Catalog #24711-364, Rochester, N.Y.), hematin (porcine) (Sigma catalog #H-3281, St. Louis, Mo.), hydrochloric acid (HCl) (VWR Catalog #VW3110-3, Rochester, N.Y.), Kim Wipes (Kimberly Clark Catalog #34256, Roswell, Ga.), microfuge tubes, 1.7 mL (VWR Catalog #20172-698, Rochester, N.Y.), NaOH (Sigma Catalog #S-5881, St. Louis, Mo.), pipet tips for 0.5 to 10 µL pipettor (VWR Catalog#53509-138, Rochester, N.Y.), pipet tips for 100–1000 µL pipettor (VWR Catolog #53512-294, Rochester, N.Y.), pipet tips for 2–20 µL and 20–200 µL pipettors (VWR Catolog #53512-260, Rochester, N.Y.), prostaglandin E2 (Sigma Catalog #P-5640, St. Louis, Mo.), prostaglandin F2alpha (Sigma Catalog #P-0424, St. Louis, Mo.), stir bar, magnetic (VWR Catalog #58948-193, Rochester, N.Y.), storage bottle, 1000 mL (Corning Catalog #1395-1L, Corning, N.Y.), storage bottle, 100 mL (Corning Catalog #1395-100, Corning, N.Y.), $CO_2$ extract of hops (Hopunion, Yakima, Wash.), Tris-HCl (Sigma Catalog #T-5941, St. Louis, Mo.), ultra-pure water (Resistance=18 megaOhm−cm deionized water).

General Procedure—Oxygen-free 1.0M Tris-HCl buffer (pH 8.0) was prepared as follows. In a 1000 mL beaker, 12.1 g Trizma HCl was dissolved into 900 mL ultra-pure water. The beaker was placed on a stir plate with a stir bar. NaOH was added until the pH reached 8.0. The volume was adjusted to a final volume of 1000 mL and stored in a 1000 mL storage bottle.

The Tris-HCl buffer was placed into a vacuum chamber with the top loosened and the air pump was turned on until the buffer stopped bubbling. The vacuum chamber was then turned off and the storage bottle was tightly covered. This step was repeated each time when oxygen-free Tris-HCl buffer was used.

One mL cofactor solution was prepared by adding 1.3 mg (−) epinephrine, 0.3 mg reduced glutathione and 1.3 mg hematin to 1 mL oxygen free Tris-HCl buffer. The solutions of the test material were prepared as needed. i.e. 10 mg of aspirin was weighed and dissolved into 1 mL DMSO. Enzymes, i.e. prostaglandin E2 or prostaglandin F2alpha, were dissolved in oxygen free Tris-HCl buffer as follows, i.e. on ice, 6.5 µL of enzyme at 40,000 units/mL was taken and added to 643.5 µL of oxygen free Tris-HCl buffer. This enzyme solution is enough for 60 reactions. The COX-1 enzyme solution was prepared as follows: In a 15 mL centrifuge tube, 10 µL COX-1 enzyme at 40,000 units/mL was added to oxygen free Tris-HCl with 50 µL of the cofactor solution per reaction. The mixture was incubated on ice for 5 minutes (i.e. for 60 reactions add 650 µl enzyme in oxygen free Tris-HCl buffer with 3.25 mL cofactor solution.

Sixty microliters of the enzyme solution were combined with 20 µl of the test solution in each well of a 96 well plate. Final concentrations of the test solutions were 100, 50, 25, 12.5, 6.25 and 3.12 µg/mL. The plates were preincubated on ice for 10 minutes. Twenty µL arachidonic acid (30 µM) was added and incubated for 15 minutes at 37° C.

Two M HCl was prepared by diluting 12.1 N Hcl in a 100 mL storage bottle, 83.5 mL ultra-pure water was added and then 16.5 mL 12.1 N HCl was added. It was stored in a 100 mL storage bottle and placed in the Biosafty cabinet (always add acid last). The reaction was terminated by adding 10 µL 2 M HCl. The final solution was used as the supernatant for the $PGE_2$ assay.

Determination of PGE2 Concentration in Medium

The procedure followed was that essentially described by Hamberg, M. and Samuelsson, B. (J. Biol. Chem. 1971. 246, 6713–6721); however a commercial, nonradioactive procedure was employed.

Equipment—freezer, −30° C. (Forma Model #F3797), heated stirring plate (VWR Catalog #33918-262, Rochester, N.Y.), multichannel pipettor, 12-Channel (VWR Catalog #53501-662, Rochester, N.Y.), orbital shaker platform (Scienceware #F37041-0000, Pequannock, N.J.), Pipet Aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), plate reader (Bio-tek Instruments Model #Elx800, Winooski, Vt.), PURELAB Plus Water Polishing System (U.S. Filter, Lowell, Mass.), refrigerator, 4° C. (Forma Model #F3775, Marietta, Ohio).

Chemicals, Reagents and Buffers—Prostaglandin $E_2$ EIA Kit-Monoclonal 480-well (Cayman Chemical Catalog #514010, Ann Arbor, Mich.), centrifuge tube, 50 mL, conical, sterile (VWR Catalog #20171-178, Rochester, N.Y.), Dulbecco's Modification of Eagle's Medium (DMEM) (Mediatech Catalog #10-013-CV, Herndon, Va.), graduated cylinder, 100 mL (VWR Catalog #24711-310, Rochester, N.Y.), Kim Wipes (Kimberly Clark Catalog #34256, Roswell, Ga.), microfuge tubes, 1.7 mL (VWR Catalog #20172-698, Rochester, N.Y.), penicillin/streptomycin (Mediatech Catalog #30-001-Cl, Hemdon, Va.), pipet tips for 0.5 to 10 µL pipettor (VWR Catolog #53509-138, Rochester, N.Y.), pipet tips for 100–1000 µL pipettor (VWR Catolog #53512-294, Rochester, N.Y.), pipet tips for 2–20 µL and 20–200 µL pipettors (VWR Catolog #53512-260, Rochester, N.Y.), pipets, 25 mL (Becton Dickinson Catalog #7551, Marietta, Ohio), storage bottle, 100 mL (Corning Catalog #1395-100, Corning, N.Y.), storage bottle, 1000 mL (Corning Catalog #1395-1L, Corning, N.Y.), ultra-pure water (Resistance=18 megaOhm–cm deionized water).

General Procedure—EIA Buffer was prepared by diluting the contents of the EIA Buffer Concentrate (vial #4) with 90 ml of Ultra-pure water. Vial #4 was rinsed several times to ensure all crystals had been removed and was then placed into a 100 mL storage bottle and stored at 4° C.

The Wash Buffer was prepared by diluting Wash Buffer Concentrate (vial #5) 1:400 with Ultra-pure water. 0.5 ml/liter of Tween 20 (vial #5a) was then added (using a syringe for accurate measurement). For one liter Wash Buffer add 2.5 ml Wash Buffer Concentrate, 0.5 ml Tween-20, and 997 ml Ultra-pure water. The solution was stored in a 1 liter storage bottle at 4° C.

The Prostaglandin $E_2$ standard was reconstituted as follows. A 200 µL pipet tip was equilibrated by repeatedly filling and expelling the tip several times in ethanol. The tip was used to transfer 100 µL of the $PGE_2$ Standard (vial #3) into a 1.7 mL microfuge tube. 900 µl Ultra-pure water was added to the tube and stored at 4° C., which was stable for ~6 weeks. The Prostaglandin $E_2$ acetylcholinesterase tracer was reconstituted as follows. 100 µL $PGE_2$ tracer (vial #2) was mixed with 30 mL of the EIA Buffer in a 50 mL centrifuge tube and stored at 4° C.

The Prostaglandin $E_2$ monoclonal antibody was reconstituted as follows. 100 L $PGE_2$ Antibody (vial #1) was mixed with 30 mL of the EIA buffer in a 50 mL centrifuge tube and stored at 4° C.

DMEM with penicillin/streptomycin was prepared by adding 5 mL penicillin/streptomycin into 500 mL DMEM and stored at 4° C.

The plates were set up as follows: Each plate contained a minimum of two blanks (B), two non-specific binding wells (NSB), two maximum binding wells ($B_0$), and an eight point standard curve run in duplicate (S1–S8). Each sample was assayed at a minimum of two dilutions and each dilution was run in duplicate.

The standard was prepared as follows: Eight 1.7 mL microuge tubes were labeled as tube 1–8. 900 µL DMEM into was put in tube 1 and 500 µL DMEM into tubes 2–8. 100 µL of the $PGE_2$ standard was put into tube 1 and mixed. Five-hundred mL of solution was taken from tube 1 and put into tube 2, and this process was repeated through tube 8.

Fifty mL EIA Buffer and 50 µl DMEM were added into the NSB wells. Fifty µl DMEM was added to the $B_0$ wells. Fifty mL of solution was taken from tube #8 and added to both the lowest standard wells (S8). Fifty mL was taken from tube #7 and added to each of the next two wells. This was continued through to tube #1. (the same pipet tip was used for all 8 of the standards making sure to equilibrate the tip in each new standard by pipeting up and down in that standard. Using a P200, 50 µl of each sample at each dilution was added to the sample wells.

Using a 12 channel pipetor, 50 µl of the Prostaglandin $E_2$ acetylcholinesterase tracer was added to each well except the Total Activity (TA) and the Blank (B) wells. Using the 12 channel pipetor, 50 µl of the Prostaglandin $E_2$ monoclonal antibody was added to each well except the Total Activity (TA), the (NSB), and the Blank (B) wells. The plate was covered with plastic film (item #7) and incubated for 18 hours at 4° C.

The plates were developed as follows: one 100 µL vial of Ellman's Reagent (vial #8) was reconstituted with 50 ml of Ultra-pure water in a 50 mL centrifuge tube. It was protected from light and used the same day. The wells were washed and rinsed five times with Wash Buffer using a 12 channel pipettor. Two-hundred mL of Ellman's Reagent was added to each well using a 12 channel pipettor and 5 µl of Tracer to the total activity(TA) wells was then added to each well using a P10 pipette. The plate was covered with a plastic film and placed on orbital shaker in the dark for 60–90 minutes.

The plate was read in the Bio-tek plate reader at a single wavelength between 405 and 420 nm. Before reading each plate, the bottom was wiped with a Kim wipe. The plate should be read when the absorbance of the wells is in the range of 0.3–0.8 A.U. If the absorbance of the wells exceeded 1.5, they were washed and fresh Ellmans' Reagent was added and then redevelop.

Calculation of Synergy and Combination Index

Synergy between the curcuminoids and andrographolide was assessed using CalcuSyn (BIOSOFT, biosoft.com). This statistical package performs multiple drug dose-effect calculations using the Median Effect methods described by T-C Chou and P. Talaly (Trends Pharmacol. Sci. 4:450–454), hereby incorporated by reference.

Briefly, it correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a plot of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85.

Synergy of test components is quantified using the combination index (CI) parameter. The CI of Chou-Talaly is based on the multiple drug-effect and is derived from enzyme kinetic models (Chou, T.-C. and Talalay, P. (1977)

A simple generalized equation for the analysis of multiple inhibitions of Michaelis-Menten kinetic systems. J. Biol. Chem. 252:6438–6442). The equation determines only the additive effect rather than synergism or antagonism. However, synergism is defined as a more than expected additive effect, and antagonism as a less than expected additive effect as proposed by Cho and Talalay in 1983 (Trends Pharmacol. Sci. (1983) 4:450–454). Using the designation of CI=1 as the additive effect we obtain for mutually exclusive compounds that have the same mode of action or for mutually non-exclusive drugs that have totally independent modes of action the following relationships: CI<1, =1, and >1 indicate synergism, additively and antagonism, respectively.

Expected median inhibitory concentrations of the two-component combinations were estimated using the relationship:

[1/Expected $IC_{50}$]=[$A/IC_{50}A$]+[$B/IC_{50}B$]

where A=mole fraction of component A in the combination and B=the mole fraction of component B in the combination.

TABLE 3 illustrates the observed and expected median inhibitory concentrations for curcumin and andrographolide for PGE2 production by COX-2 in the RAW 264.7 cell assay. While the expected $IC_{50}$ for the 1:4 combination of curcumin was 21.1 µg/mL, the observed value was 0.26 µg/mL or 80.8-fold greater. This level of difference was unexpected and constitutes a novel finding for the combined COX-2 inhibitory activity of the 1:4 combination of curcumin and andrographolide.

TABLE 5

COX-2 Specificity for a 1:4 Formulation of Curcumin and Andrographolide

| TEST MATERIAL | COX-1 $IC_{50}$ [µg/mL] | COX-2 $IC_{50}$ [µg/mL] | SPECIFICIY COX-1/COX-2 |
|---|---|---|---|
| Curcumin | 12.6 | 4.5 | 2.8 |
| Andrographolide | 1500 | 287 | 5.2 |
| Curcumin/Andrographolide (1:4) | 17.6 | 0.28 | 63 |

The medium inhibitory concentration of COX-2 by curcumin alone in the RAW 264.7 cell model was 4.5 µg/mL (TABLE 5). Inhibition of COX-1 enzyme activity by curcumin was somewhat higher with an $IC_{50}$ of 12.6 µg/mL. Andrographolide exhibited an $IC_{50}$ of COX-2 protein expression of 287 µg/mL and an $IC_{50}$ for COX-1 enzyme inhibition estimated at 1500 µg/mL; the COX-2 specificity of curcumin alone was 2.8 and for andrographolide, it was 5.2. A 1:4 formulation of curcumin and andrographolide unexpectedly increased the COX-2 specificity to 63. This finding indicates that combinations of curcumin and andrographolide could function as potent anti-inflammatory formulations without the GI side effects seen with COX-1 inhibition.

TABLE 3

Observed and Expected Median Inhibitory Concentrations for a Formulation of Curcumin and Andrographolide

| First Compound | First Compound $IC_{50}$ (µg/ml) | Second Compound | Second Compound (Ratio) | Second Compound $IC_{50}$ (µg/ml) | First $IC_{50}$ (µg 1st/mL) | Second $IC_{50}$ (µg 2nd/mL) | Observed $IC_{50}$ (µg mix/mL) | Expected $IC_{50}$ (µg mix/mL) |
|---|---|---|---|---|---|---|---|---|
| Cuccumin 1 | 4.50 | Andrographolide | 4 | 267 | 0.052 | 0.208 | 0.260 | 21.079 |

Statistical analysis of inhibition of COX-2 production of PGE2 in the RAW 264.7 cell model for the 1:4 combination of curcumin and andrographolide is presented in TABLE 4. The CI for this combination was 0.551, 0.546 and 0.542, respectively, for the $IC_{50}$, $IC_{75}$ and $IC_{90}$. These CI values indicate strong synergy between curcumin and andrographolide over the complete dose-response curve.

TABLE 4

Combination Index for a 1:4 Formulation of Curcumin and Andrographolide

| Combination Index | | | |
|---|---|---|---|
| $IC_{50}$ | $IC_{75}$ | $IC_{90}$ | Mean CI |
| 0.551 | 0.546 | 0.542 | 0.546 |

EXAMPLE 2

Synergistic Inhibition of Prostaglandin E2 Production and Increased COX-2 Specificity of Curcuminoids with Ursolic Acid This example illustrates the effect of ursolic acid on curcuminoid inhibition of PGE2 production in cultured RAW 264.7 cells 24 hours following LPS stimulation. The experiment was performed as described in EXAMPLE 1, except that the second compound is ursolic acid, which may be obtained from Sigma (St. Louis, Mo.).

TABLE 6 illustrates the observed and expected median inhibitory concentrations for curcumin and ursolic acid for PGE2 production by COX-2 in the RAW 264.7 cell assay. While the expected $IC_{50}$ for the 1:2 combination of curcumin was 12.1 µg/mL, the observed value was 6.6 µg/mL or 1.8-fold greater. This level of difference was unexpected and constitutes a novel finding for the combined COX-2 inhibitory activity of the 1:2 combination of curcumin and ursolic acid.

TABLE 6

Observed and Expected Median Inhibitory Concentrations for a Formulation of Curcumin and Ursolic Acid

| First Compound | First Compound IC$_{50}$ (µg/ml) | Second Compound | Second Compound (Ratio) | Second Compound IC$_{50}$ (µg/ml) | Combined | | | |
|---|---|---|---|---|---|---|---|---|
| | | | | | First IC$_{50}$ (µg 1st/mL) | Second IC$_{50}$ (µg 2nd/mL) | Observed IC$_{50}$ (µg mix/mL) | Expected IC$_{50}$ (µg mix/mL) |
| Curcumin 1 | 4.5 | Ursolic Acid | 2 | 78 | 2.190 | 4.38 | 6.570 | 12.103 |

Statistical analysis of inhibition of COX-2 production of PGE2 in the RAW 264.7 cell model for the 1:2 combination of curcumin and ursolic acid is presented in TABLE 7. The CI for this combination was 0.583, 0.688 and 0.874, respectively, for the IC$_{50}$, IC$_{75}$ and IC$_{90}$. These CI values indicate strong synergy between curcumin and ursolic acid over the complete dose-response curve.

TABLE 7

Combination Index for a 1:2 Formulation of Curcumin and Ursolic Acid

| Combination Index | | | |
|---|---|---|---|
| IC$_{50}$ | IC$_{75}$ | IC$_{90}$ | Mean CI |
| 0.583 | 0.688 | 0.874 | 0.715 |

The medium inhibitory concentration of COX-2 by curcumin alone in the RAW 264.7 cell model was 4.5 µg/mL. Inhibition of COX-1 enzyme activity by curcumin was somewhat higher with an IC$_{50}$ of 12.6 µg/mL. Ursolic acid exhibited an IC$_{50}$ of COX-2 protein expression of 59.4 µg/mL and an IC$_{50}$ for COX-1 enzyme inhibition estimated at 99.6 µg/mL; the COX-2 specificity of curcumin alone was 2.8 and for ursolic acid, it was 1.67. A 1:2 formulation of curcumin and ursolic acid unexpectedly increased the COX-2 specificity to 25.7. This finding indicates that combinations of curcumin and ursolic acid could function as potent anti-inflammatory formulations without the GI side effects seen with COX-1 inhibition.

TABLE 8

COX-2 Specificity for a 1:2 Formulation of Curcumin and Ursolic Acid

| TEST MATERIAL | COX-1 IC$_{50}$ [µg/mL] | COX-2 IC$_{50}$ [µg/mL] | SPECIFICIY COX-1/COX-2 |
|---|---|---|---|
| Curcumin | 12.6 | 4.5 | 2.8 |
| Ursolic Acid | 99.6 | 59.4 | 1.67 |
| Curcumin/Ursolic Acid (1:2) | 170 | 6.6 | 25.7 |

EXAMPLE 3

Synergistic Inhibition of Prostaglandin E2 Production in Murine B Cells by Curcuminoids and Oleanolic Acid This example illustrates the effect of curcuminoids and oleanolic acid on PGE2 production in cultured RAW 264.7 cells 24 hours following LPS stimulation. The experiment is performed as described in EXAMPLE 1, except that the second compound is oleanolic acid, which may be obtained from Sigma (St. Louis, Mo.).

TABLE 9 illustrates the observed and expected median inhibitory concentrations for curcumin and oleanolic acid for PGE2 production by COX-2 in the RAW 264.7 cell assay. While the expected IC$_{50}$ for the 1:2 combination of curcumin was 13.1 gg/mL, the observed value was 5.8 µg/mL or 2.25-fold greater. This level of difference was unexpected and constitutes a novel finding for the combined COX-2 inhibitory activity of the 1:2 combination of curcumin and oleanolic acid.

Statistical analysis of inhibition of COX-2 production of PGE2 in the RAW 264.7 cell model for the 1:2 combination of curcumin and oleanolic acid is presented in TABLE 10. The CI for this combination was 0.476, 0.720 and 1.111, respectively, for the IC$_{50}$, IC$_{75}$ and IC$_{90}$. These CI values indicate strong synergy between curcumin and oleanolic acid at concentrations below the IC$_{90}$.

TABLE 9

Observed and Expected Median Inhibitory Concentrations for a Formulation of Curcumin and Oleanolic Acid

| First Compound | First Component IC$_{50}$ (µg/ml) | Second Compound | Second Component (Ratio) | Second Component IC$_{50}$ (µg/ml) | Combined | | | |
|---|---|---|---|---|---|---|---|---|
| | | | | | First IC$_{50}$ (µg 1st/mL) | Second IC$_{50}$ (µg 2nd/mL) | Observed IC$_{50}$ (µg mix/mL) | Expected IC$_{50}$ (µg mix/mL) |
| Curcumin 1 | 4.5 | Oleanolic Acid | 2 | 385 | 1.930 | 3.87 | 5.800 | 13.192 |

The medium inhibitory concentration of COX-2 by curcumin alone in the RAW 264.7 cell model was 4.5 μg/mL. Inhibition of COX-1 enzyme activity by curcumin was somewhat higher with an $IC_{50}$ of 12.6 μg/mL. Oleanolic acid exhibited an $IC_{50}$ of COX-2 protein expression of 134 μg/mL and an $IC_{50}$ for COX-1 enzyme inhibition estimated at 168 μg/mL; the COX-2 specificity of curcumin alone was 2.8 and for oleanolic acid, it was 1.25. A 1:2 formulation of curcumin and oleanolic acid unexpectedly increased the COX-2 specificity to 95.2. This finding indicates that combinations of curcumin and oleanolic acid could function as potent anti-inflammatory formulations without GI side effects due to COX-1 inhibition.

TABLE 10

Combination Index for a 1:2 Formulation of Curcumin and Oleanolic Acid

| Combination Index | | | |
| --- | --- | --- | --- |
| $IC_{50}$ | $IC_{75}$ | $IC_{90}$ | Mean CI |
| 0.476 | 0.72 | 1.111 | 0.769 |

The medium inhibitory concentration of COX-2 by curcumin alone in the RAW 264.7 cell model was 4.5 μg/mL. Inhibition of COX-1 enzyme activity by curcumin was somewhat higher with an $IC_{50}$ of 12.6 μg/mL. Oleanolic acid exhibited an $IC_{50}$ of COX-2 protein expression of 134 μg/mL and an $IC_{50}$ for COX-1 enzyme inhibition estimated at 168 μg/mL; the COX-2 specificity of curcumin alone was 2.8 and for oleanolic acid, it was 1.25. A 1:2 formulation of curcumin and oleanolic acid unexpectedly increased the COX-2 specificity to 95.2. This finding indicates that combinations of curcumin and oleanolic acid could function as potent anti-inflammatory formulations without the GI side effects seen with COX-1 inhibition.

TABLE 11

COX-2 Specificity for a 1:2 Formulation of Curcumin and Oleanolic Acid

| TEST MATERIAL | COX-1 $IC_{50}$ [μg/mL] | COX-2 $IC_{50}$ [μg/mL] | SPECIFICIY COX-1/COX-2 |
| --- | --- | --- | --- |
| Curcumin | 12.6 | 4.5 | 2.80 |
| Oleanolic Acid | 168 | 134 | 1.25 |
| Curcumin/Oleanolic Acid (1:2) | 257 | 2.7 | 95.2 |

EXAMPLE 4

Normalization of Joint Functioning Following Trauma

A representative composition of the present invention as a dietary supplement would be in an oral formulation, i.e. tablets, that would supply one of the following combinations: (a) 15 mg curcuminoid/kg per day and 6.0 mg andrographolide/kg per day; (b) 15 mg curcuminoid/kg per day and 6.0 mg ursolic acid/kg per day; (c) 15 mg curcuminoid/kg per day and 6.0 mg oleanolic acid/kg per day. Normalization of joint movement following physical trauma due to exercise or repetitive movement stress would be expected to occur following two to ten doses. This result would be expected in all animals.

EXAMPLE 5

Clinical Effectiveness of Lotion Formulations in the Treatment of Acne Rosacea

A lotion designed to contain one of the following: (a) 0.1% wt curcuminoids and 0.5% andrographolide; (b) 0.1% wt curcuminoids and 0.5% ursolic acid; or (c) 0.1% wt curcuminoids and 0.5% oleanolic acid, is applied to affected areas of patients who have exhibited acne rosace as diagnosed by their health practitioner and confirmed by an independent board-certified dermatologist. Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the combination composition of the present invention in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

EXAMPLE 6

Clinical Effectiveness of Lotion Formulation in the Treatment of Psoriasis

This example is performed in the same manner as described in Example 5, except that the composition is applied to affected areas of patients who have exhibited psoriasis as diagnosed by their own practitioner and confirmed by an independent board-certified dermatologist. Self-evaluation tests are administered one week prior to the study to quantify the surface area affected and skin condition. In addition, similar variables are scored by the professional clinical staff not aware of the patients treatment status. These evaluations are repeated on Days 0, 7, 30 and 60.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the combination of a curcuminoid and a second compound selected from the group consisting of andrographolide, ursolic acid and oleanolic acid lotion formulation are considered improved if the patients' scores improve by greater than 20% from the pre-test scores within each category evaluated. The percentage of persons exhibiting improvement is compared between the curcuminoid combining with a second compound selected from the group consisting of andrographolide, ursolic acid and oleanolic acid formulations and the placebo control. The difference between the two groups is considered statistically significant if the probability of rejecting the null hypothesis when true is less than five percent.

EXAMPLE 7

Clinical Effectiveness of a Formulation in the Treatment of Alzheimer's Disease

An oral formulation as described in Example 4 is administered to patients who have manifested an early stage of Alzheimer's Disease (AD), as diagnosed by their practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is significant deterioration in the test scores during the course of the clinical trial. Patients treated with the curcuminoids combining with a second compound selected from the group consisting of andrographolide, ursolic acid and oleanolic acid formulation are considered improved if the patients' scores remain the same or improve during the course of the clinical trial.

EXAMPLE 8

Oral Formulation in the Treatment and Prevention of Colon Cancer

An oral formulation as described in Example 4 is administered to patients who have manifested an early stage of colon cancer as diagnosed by their own practitioner and confirmed by a independent board-certified oncologist.

Patients are randomly assigned to the test formulation or a placebo at the start of the study. The test formulation and placebo are taken orally one or two times per day. Treatment for conditions such as diabetes, hypertension, etc. is allowed during the study. Endoscopic evaluations are made at one, two, six and twelve months. Evidence of reappearance of the tumor during any one of the four follow-up clinical visits is considered a treatment failure. The percentage of treatment failures is compared between the curcuminoids combining with a second compound selected from the group consisting of andrographolide, ursolic acid and oleanolic acid formulation and the placebo control. The difference between the two groups is considered statistically significant if the probability of rejecting the null hypothesis when true is less than five percent.

EXAMPLE 9

Oral Formulation for the Treatment of Irritable Bowel Syndrome

An oral formulation as described in Example 4 is administered to patients who have manifested irritable bowel syndrome as diagnosed by their practitioner. Normal bowel functioning is restored within 24 hours.

EXAMPLE 10

Normalization of Joint Functioning in Osteoarthritis

Using compositions described in Example 4 normalization of joint stiffniess due to osteoarthritis occurs following five to twenty doses, in the presence or absence of glucosamine or chondroitin sulfate. In addition, the composition does not interfere with the normal joint rebuilding effects of these two proteoglycan constituents, unlike traditional non-steroidal anti-inflammatory agents.

In summary, one embodiment of the present invention is a composition for inhibition of inducible COX-2 activity and having minimal effect on COX-1 activity. The composition comprises, as a first component an effective amount of a curcuminoid species and an effective amount of a second component selected from the group consisting of a diterpene lactone species and a triterpene species or derivatives thereof. The curcuminoid species is curcumin, demethoxycurcurmin, or bisdemethoxycurcumin. The diterpene lactone species is andrographolide, dehydroandrographolide, deoxyandrographolide, neoandrographolide, selenoandrographolide, homoandrographolide, andrographan, amdrographon, andrographosterin, 14-deoxy-11-oxoandrographolide, 14-deoxy-11,12-didehydroandrographolide, andrographiside, or edelin lactone. The triterpene species is a member selected from the group consisting of ursolic acid, oleanolic acid, betulin, betulinic acid, glycyrrhetinic acid, glycyrrhizic acid, triperin, 2,3,-dihydroxyurs-12-3n-28-oic acid, 2,-hydroxyursolic acid, 3-oxo-ursolic acid, celastrol, friedelin, tritophenolide, uvaol, eburicoic acid, glycyrrhizin, gypsogenin, oleanolic acid-3-acetate, pachymic acid, pinicolic acid, sophoradiol, soyasapogenol A, soyasapogenol B, tumulosic acid, ursolic acid-3-acetate or sitosterol. The first or the second components of the present composition may be of pharmaceutical grade or derived from plant(s) or plant extract(s). The first or second components may also be conjugated with a compound such as mono- or di-saccharides, amino acids, sulfates, succinate, acetate or glutathione. The compositions of the present invention may be formulated in a pharmaceutically acceptable carrier and contain additives such as antioxidants, vitamins, minerals proteins, fats, carbohydrates, glucosamine, chondrotin sulfate or aminosugars.

Other embodiments of the present invention include methods of dietary supplementation in animals suffering symptoms of inflammation the compositions of the present invention to reduce the symptoms. The composition is formulated in a dosage form such that said administration provides from 0.001 to 30.0 mg body weight per day of each curcuminoid species, and from 0.5 to 20.0 mg/kg bodyweight per day of each diterpene lactones species or triterpenes species. The composition is administered in an amount sufficient to maintain a serum concentration of 0.1 to 50 $\mu$M of each curcuminoid species, and from 0.001 to 50 $\mu$M of each diterpene lactone species or triterpene species. The animal may be humans, non-human primates, dogs, cats, birds, reptiles, amphibians, horses or ruminants. The administration may be a oral, parenteral, topical, transdermal or transmucosal delivery.

Thus, among the various formulations taught there has been disclosed a formulation comprising curcuminoids, as the first component, and a second component selected from the group consisting of andrographolide, ursolic acid and oleanolic acid, as the second component. These combinations provide for a synergistic anti-inflammatory effect in response to physical or chemical injury or abnormal immune stimulation due to a biological agent or unknown etiology.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the present invention disclosed above.

We claim:

1. A composition comprising an effective amount of curcumin and an effective amount of andrographolide, wherein the ratio of curcumin and andrographolide is from 1:10 to 10:1, said composition having at least 5 times less inhibitory activity on cyclooxygenase-1 (COX-1) than on cyclooxygenase-2 (COX-2).

2. The composition of claim 1, wherein the curcumin is pharmaceutical grade curcumin.

3. The composition of claim 1, wherein the andrographolide is pharmaceutical grade andrographolide.

4. The composition of claim 1, wherein at least one of the curcumin or andrographolide is derived from a plant or plant extract.

5. The composition of claim 1, wherein at least one of the curcumin or andrographolide is conjugated with a compound selected from the group consisting of mono- or disaccharides, amino acids, sulfates, succinate, acetate and glutathione.

6. The composition of claim 5, wherein the conjugated compound is mono- or disaccharide.

7. The composition of claim 1, said composition further comprising one or more members selected from the group consisting of antioxidants, vitamins, minerals, proteins, fats, carbohydrates, glucosamine, chondrotin sulfate and amino-sugars.

8. The composition of claim 7, wherein said composition further comprises glucosamine.

9. A composition comprising an effective amount of curcumin and an effective amount of oleanolic acid, wherein the ratio of curcumin and oleanolic acid is from 1:10 to 10:1, said composition having at least 5 times less inhibitory activity on cyclooxygenase-1 (COX-1) than on cyclooxygenase-2 (COX-2).

10. The composition of claim 9, wherein the curcumin is pharmaceutical grade curcumin.

11. The composition of claim 9, wherein the oleanolic acid is pharmaceutical grade oleanolic acid.

12. The composition of claim 9, wherein at least one of the curcumin or oleanolic acid is derived from a plant or plant extract.

13. The composition of claim 9, wherein at least one of the curcumin or oleanolic acid is conjugated with a compound selected from the group consisting of mono- or di-saccharides, amino acids, sulfates, succinate, acetate and glutathione.

14. The composition of claim 13, wherein the conjugated compound is mono- or di-saccharide.

15. The composition of claim 9, said composition further comprising one or more members selected from the group consisting of antioxidants, vitamins, minerals, proteins, fats, carbohydrates, glucosamine, chondrotin sulfate and amino-sugars.

16. The composition of claim 15, wherein said composition further comprises glucosamine.

* * * * *